US012678211B2

(12) United States Patent　　　(10) Patent No.: US 12,678,211 B2
Kažič et al.　　　　　　　　　　　(45) Date of Patent: Jul. 14, 2026

(54) DIRECTIONAL MICRO-PULSED LIQUID SPRAY FOR COOLING

(71) Applicant: Fotona d.o.o., Ljubljana (SI)

(72) Inventors: Marko Kažič, Dob pri Domžalah (SI); Matjaž Lukač, Ljubljana (SI); Nejc Lukač, Ljubljana (GI); Blaž Tasič Muc, Kamnik (GI)

(73) Assignee: Fotona d.o.o., Ljubljana (SI)

( * ) Notice: Subject to any disclaimer, the term of this patent is extended or adjusted under 35 U.S.C. 154(b) by 283 days.

(21) Appl. No.: 18/531,921

(22) Filed: Dec. 7, 2023

(65) Prior Publication Data

US 2024/0189010 A1　Jun. 13, 2024

(30) Foreign Application Priority Data

Dec. 7, 2022　(EP) ..................................... 22211909

(51) Int. Cl.
　　*A61B 18/02*　　(2006.01)
　　*A61B 18/20*　　(2006.01)
　　A61B 18/22　　(2006.01)
(52) U.S. Cl.
　　CPC ........ *A61B 18/0218* (2013.01); *A61B 18/203* (2013.01); *A61B 2018/2253* (2017.05)
(58) Field of Classification Search
　　CPC ... A61B 18/0218; A61B 18/203; A61B 18/00; A61B 2018/2253; A61B 2018/00452; A61B 2018/00029; A61B 2018/00011;

B05B 7/0815; B05B 7/2491; B05B 12/04; B05B 15/68; A61M 2205/50; A61M 11/02; A61M 19/00; A61M 2202/02; A61M 2202/04; A61M 2210/04; A61F 7/00; A61F 2007/0063; A61D 7/00
See application file for complete search history.

(56) References Cited

U.S. PATENT DOCUMENTS

2018/0169688 A1　6/2018　Medard et al.
2018/0214207 A1*　8/2018　Deibel ............... A61B 17/3203
2019/0239938 A1*　8/2019　Kazic ................... A61N 5/0616

FOREIGN PATENT DOCUMENTS

EP　　　3520728 A1　　8/2019

* cited by examiner

*Primary Examiner* — Ankit D Tejani
*Assistant Examiner* — Joshua Brendon Solomon
(74) *Attorney, Agent, or Firm* — Renner, Otto, Boisselle & Sklar, LLP

(57)　　　　　ABSTRACT

A nozzle assembly for cooling a treatment area with a fluid comprises a first fluid outlet and a second fluid outlet operable individually as well as simultaneously and arranged apart such that the fluid covers a first portion of the treatment area if only the first fluid outlet is operated, a second portion of the treatment area if only the second fluid outlet is operated (wherein the second portion is not fully contained in the first portion), and a third portion of the treatment area if both the first fluid outlet and the second fluid outlet are operated (wherein the third portion is not fully contained in the first portion and/or the second portion).

19 Claims, 7 Drawing Sheets

DIRECTIONAL MICRO-PULSED LIQUID SPRAY FOR COOLING

Figure 1:
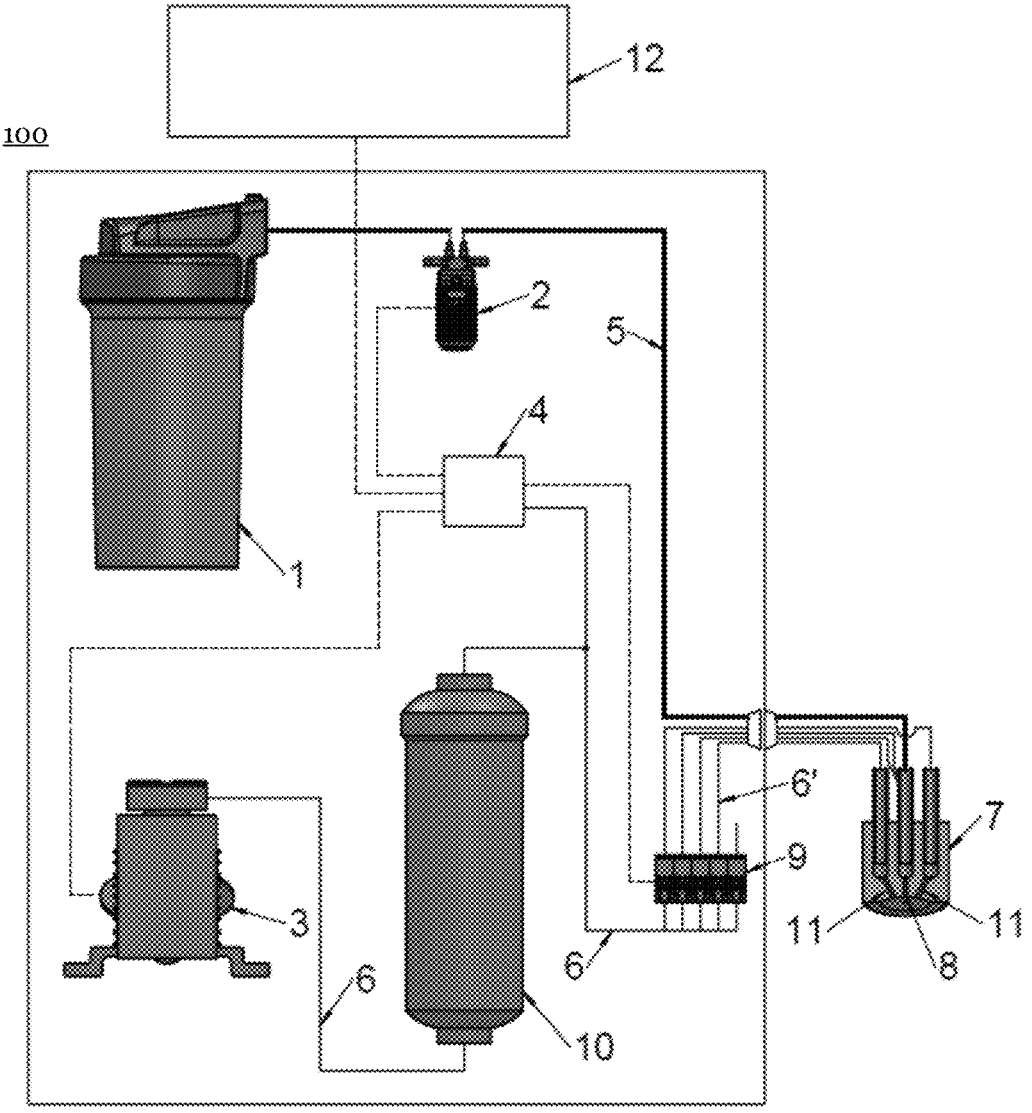

This application claims priority to European Patent Application No. 22211909.1, filed Dec. 7, 2022, which is hereby incorporated herein by reference in its entirety.

FIELD OF THE INVENTION

The present invention relates to a system and a method for cooling surfaces, in particular for cooling surfaces of human or animal tissues which are treated with an energy-based medical device such as a laser, an intense pulse light device or a radio frequency device.

TECHNICAL BACKGROUND

In the following, only medical and biological applications will be discussed, but the invention is also directed towards industrial or other applications where fast cooling of surfaces is required.

In medical applications where energy is delivered to the tissue for heating, coagulation or destruction of targets, a non-specific heating of the tissue surface (such as the epidermis) is a common side effect. Energy-based medical devices include, for example, a laser, an intense pulse light (IPL) device or a radio frequency (rf) device. In what follows, the words "laser", "laser pulse", "laser beam" etc. will be used from time to time to represent any type of such energy-based devices.

In treatments using energy-based medical devices, a certain amount of energy needs to be delivered, in order to achieve the desired effect on the target chromophore or target structure. For example, in applications for hair removal by means of a laser, enough laser fluence (energy/area) needs to be delivered to the hair bulb in order to achieve its destruction, but, at the same time, epidermal damage should be minimized. As many laser wavelengths, especially the ones which penetrate the skin surface, are absorbed in melanin (which is abundantly present in the epidermis), heating of the epidermis is an inevitable side effect of many laser treatments. Often, the threshold fluence which is needed for destroying the target chromophore or structure is very close to the fluence threshold for epidermal injury. Besides, uncontrolled heating of the epidermis above its coagulation temperature of 65 to 70° C. for a prolonged period of time can induce acute epidermal damage or blistering and can also lead to scarring and hypopigmentation. In order to avoid these complications, while at the same time allowing enough energy to be delivered to the target structure, cooling of the epidermal surface layer is necessary.

Exemplary applications where high energies are used and cooling is necessary for avoiding epidermal damage include laser hair removal, coagulation of veins and vascular lesions. In other applications, e.g., non-invasive fat reduction, relatively low energy densities are delivered during a prolonged exposure to a laser, a radio frequency device, or another energy source which leads to a prolonged heating of the subdermal fat to temperatures above 42° C. This causes an apoptosis of adipose cells and a reduction of the fat layer. In these methods, epidermal cooling may be used for avoiding a prolonged heating of the epidermis, thus maximizing patient safety and comfort.

In treatments with energy-based medical devices, the problem of epidermal overheating is overcome by cooling the epidermis prior, during and/or after the treatment. An ideal cooling method should efficiently lower the temperature of the epidermal surface layer only, since cooling of deeper layers would interfere with the desired heating of the target structure/chromophore. In particular, if deeper layers of the tissue were also cooled, it would be necessary to deliver higher energies to the target structure/chromophore for obtaining the desired temperature.

Different types of cooling systems are regularly used in medical systems, wherein different types of cooling mediums are brought in contact with the tissue surface. The most common methods include contact cooling with a chilled surface of a cooling device, cooling by means of a cryogen spray and cooling with cold air.

Contact cooling using a cooled glass or metal surface is commonly used and achieves localized and rapid cooling. However, this method is disadvantageous if cooling is needed for a prolonged period of time since the prolonged exposure to a cold plate (which is normally kept at a low temperature by an active delivery of another cooling medium such as a liquid coolant) leads to cooling of deeper tissue layers and of the target structure. However, as already mentioned above, the cooling of deeper layers leads to an increase in the energy needed for target destruction. Besides, contact cooling methods can also result in skin compression which, in some application, influences the absorption of the target chromophore, e.g., in the case of the removal of vascular lesions. Furthermore, contact cooling may often lead to areas being cooled that do not require cooling, in turn diminishing cooling efficiency.

Cooling by means of a cryogen spray is another commonly used method. In this cooling method, a cryogen spray is sprayed shortly before the delivery of the laser pulse, thus minimizing the exposure of the skin to the cryogen spray which cools to very low temperatures. This method is efficient for epidermal protection when high fluences are used. However, side effects from excessive skin cooling, such as hypopigmentation and skin irritations, have been reported. Already for this reason, cryogen sprays are rather unsuitable for cooling larger areas as is required, e.g., in hair removal treatments. Besides, cryogen sprays are also harmful to the environment since they have a high global warming potential. Due to these safety hazards, the storage and distribution of (refrigerants used in) cryogen sprays is often complicated and expensive.

Cold air cooling is often used in laser treatments, wherein cold air is directed to the treatment area before and during the laser treatment. The disadvantage of cold air cooling is the relative inefficiency of the medium air for cooling tissues, thus requiring long exposure times. This can lead to patient discomfort and to cooling of deeper layers (which, as mentioned before, adversely impacts the threshold fluence needed for the destruction of the target chromophore).

A water-based spray has previously only been commonly used in dental laser applications, mainly for moistening the tissues, debris removal and as an aid for a more efficient ablation. However, a water-based spray has previously not been commonly used for cooling tissue surfaces, especially not for cooling skin surfaces. The reason for this is that the commonly available liquid sprays, such as the ones used by dental lasers, operate continuously and hence would generate a liquid film on the skin surface which would act as a thermal barrier for the heat transfer. In particular, if a liquid film is present, a quick evaporation of liquid droplets can no longer take place, thus preventing efficient cooling. To avoid the formation of an undesirable liquid film, the liquid has to be in constant flow. In particular, the liquid has to be constantly removed from the treatment area. A removal of the liquid by means of a suction device can be relatively easily achieved in an enclosed treatment area which is already wet, such as the mouth, but becomes very impractical when trying to cool large body surfaces. In addition, in many dermatological applications such as hair removal, skin tightening and fat reduction, an effective and homogeneous cooling of large skin areas of up to about 5000 cm$^2$ or even 10000 cm$^2$ is required which represents a considerable technical challenge when liquid spray cooling is used.

European Patent application EP 3 520 728 A1 tackles at least the first of these problems by means of a micro-pulsed spray for cooling. More specifically, it discloses an apparatus for cooling tissues which are treated with an energy-based device, such as a laser. The apparatus comprises a spray nozzle which generates an atomized liquid spray for the treatment area, wherein the atomized liquid spray is based on a mixture of liquid and gas. Further, the spray nozzle comprises at least one liquid outlet which ejects a liquid, and at least one gas outlet which ejects a gas stream. Next to at least one delivery means for delivering pressurized gas to the spray nozzle, the apparatus also comprises a pumping means for the liquid. Notably, the pumping means is configured to operate in pulses. This may help avoid the generation of liquid films on the skin surface.

The present invention is concerned with a device for cooling tissues that are treated with an energy-based medical device, wherein at least some of the above-described disadvantages of the prior art are avoided and other aspects further improved.

SUMMARY OF THE INVENTION

In a first aspect, the present invention relates to a nozzle assembly for cooling a treatment area with a fluid. The nozzle assembly comprises a first fluid outlet and a second fluid outlet operable individually as well as simultaneously and arranged apart such that the fluid covers a first portion of the treatment area if only the first fluid outlet is operated, a second portion of the treatment area if only the second fluid outlet is operated, wherein the second portion is not fully contained in the first portion, and a third portion of the treatment area if both the first fluid outlet and the second fluid outlet are operated (simultaneously), wherein the third portion is not fully contained in the first portion and/or the second portion.

That is, the first fluid outlet and the second fluid outlet are arranged apart such that the fluid covers a respective, distinct portion of the treatment area if one of them is operated individually. Therein, the portion of the treatment area covered upon individual operation of the first fluid outlet (i.e., the first portion) may not fully contain the portion of the treatment area covered upon individual operation of the second fluid outlet (i.e., the second portion). In some embodiments, this may apply vice versa. In particular, in some embodiments, the first portion and the second portion may be disjunct, preferably disjunct and arranged at a distance to each other. For example, the first portion may comprise a first diameter $d_1$, which may be defined as the maximum distance between any two points (on the perimeter) of the first portion. Similarly, the second portion may comprise a second diameter $d_2$, which may be defined as the maximum distance between any two points (on the perimeter) of the second portion. A distance $d_{\overline{12}}$ at which the first portion and the second portion are arranged may be defined as the minimum distance between any one point (on the perimeter) of the first portion and any one point (on the perimeter) of the second portion. The distance $d_{\overline{12}}$ may at least be $0.1d_1$, $0.2d_1$, $0.25d_1$, $0.5d_1$ or $d_1$; and/or at least $0.1d_2$, $0.2d_2$, $0.25d_2$, $0.5d_2$ or $d_2$. Additionally or alternatively, the distance $d_2$ may at most be $d_1$, $2d_1$, $2.5d_1$, $3d_1$ or $5d_1$; and/or at most $d_2$, $2d_2$, $2.5d_2$, $3d_2$ or $5d_2$. In some embodiments, the given upper limits may represent lower limits and vice versa. Any combinations of these lower and upper limits are expressly contemplated, as far as meaningful.

Additionally, the first fluid outlet and the second fluid outlet may be operated simultaneously and are arranged apart such that, upon such simultaneous operation of both, the fluid covers a portion (i.e., the third portion) of the treatment area that is neither fully contained in the first portion or the second portion, nor in their combination (e.g., their set union). That is, the first portion and/or the second portion may not fully contain the third portion. Meanwhile, in some embodiments, the third portion may fully contain the first portion and/or the second portion. In other embodiments, the third portion may not fully contain the first portion and/or the second portion.

Throughout this disclosure, a portion of the treatment area in the above sense may be understood as the smallest possible portion of the treatment area that is covered by (e.g., receives) (at least) 50%, preferably (at least) 70%, more preferably (at least) 90%, even more preferably (at least) 95%, most preferably (at least) 99%, or even 100% of the fluid ejected from the respective fluid outlet(s).

Hence, the size and form of the area receiving cooling is adjustable. Thereby, tissue areas that are not significantly heated during the delivery of energy can be bypassed, such that in turn required cooling power can be minimized and hence cooling efficiency maximized. The nozzle assembly can be used to efficiently cool tissues of varying sizes and forms with a fluid, rendering said nozzle assembly particularly versatile as it may be applied in various treatments and/or applications.

Specifically, the first fluid outlet and the second fluid outlet are operable and arranged apart such that, upon their simultaneous operation, the fluid covers parts of the treatment area outside the first portion and/or second portion (and, optionally, parts of the first and/or second portions may no longer be covered). Put differently, the first fluid outlet and the second fluid outlet are operable and arranged such that the fluid may reach parts of the treatment area that it could/would not reach using each of the first and/or second fluid outlets individually. Thereby, the present invention allows to increase and adjust the size and shape of the treatment area without adding constructional complexity. By arranging the first and the second fluid outlet appropriately and having them operable simultaneously, additional parts of the treatment area may be reached by the fluid, however without the need for providing an additional fluid outlet. Thus, the nozzle assembly can be used to efficiently cool tissues of varying sizes and forms, allowing its use in various treatments and/or applications. At the same time, the nozzle assembly is compact and relatively simple from a constructional point of view in that it does not require an additional fluid outlet in order to have the fluid cover parts of the treatment area that the fluid may not reach upon operation of the first fluid outlet or the second fluid outlet individually.

Thereby, the present invention does not only overcome the various shortcomings of previously known cooling systems as discussed above, but it also provides an advantage over the spray nozzle disclosed in European Patent application EP 3 520 728 A1. Since the spray nozzle disclosed therein is not adapted to operate two outlets simultaneously such as to provide fluid to parts of a treatment area that may not be provided with fluid upon individual operation of the outlets, said spray nozzle may—generally speaking—effectively require a different number of outlets depending on the size and shape of the treatment area, which may render it less versatile in some applications and, depending on the application/desired treatment area, also less compact than the nozzle assembly of the present application. As a corollary, fluid outlets according to the present invention may generally be arranged differently than the outlets disclosed in EP 3 520 728 A1. In particular, fluid outlets according to the present invention may be configured to point in different directions than the outlets disclosed in EP 3 520 728 A1, such that they—upon individual operation—cover different portions of the treatment area than the outlets disclosed in EP 3 520 728 A1 (assuming, e.g., a same distance between the spray nozzle or nozzle assembly, respectively, and the treatment area). As will become particularly clear below with reference to FIG. 7, fluid outlets according to the present invention may be arranged such that the portions covered by the cooling fluid upon individual operation of these fluid outlets, taken together with the portions covered by the cooling fluid upon simultaneous operation of two or more of these fluid outlets, provide for a coverage of the treatment area that is as seamless as possible. Notably, this may allow to leave voids between the portions covered by the cooling fluid upon individual operation of the respective fluid outlets, which may in turn be arranged accordingly, e.g., such that they point to portions further from the center of the treatment area as compared to the outlets disclosed in EP 3 520 728 A1. In contrast, the outlets disclosed in EP 3 520 728 A1 may need to be arranged such that the portions covered by the cooling fluid upon their individual operation, taken alone, provide for a coverage of the treatment area that is as seamless as possible. As such, voids between said portions—and a corresponding arrangement of the outlets—may generally rather be undesirable in EP 3 520 728 A1 as this would lead to a less seamless coverage of the treatment area.

Specifically, an appropriate arrangement of the first fluid outlet and the second fluid outlet may be characterized in that a distance between a center of the first portion and the first fluid outlet is larger than a distance between the center of the first portion and the second fluid outlet, and/or in that a distance between a center of the second portion and the second fluid outlet is larger than a distance between the center of the second portion and the first fluid outlet (e.g. when the nozzle assembly is applied with a flat treatment area parallel to a line connecting the first fluid outlet and the second fluid outlet). Throughout this disclosure, a center of a portion or an area may be defined as the centroid or geometrical center of the respective portion or area. That is, in particular, the first fluid outlet and the second fluid outlet may be arranged cross-wise (with respect to the first and second portion the fluid respectively covers upon operation of these fluid outlets). That is, the direction of motion of fluid ejected from the first fluid outlet is angled (or, alternatively, skew) with respect to the direction of motion of fluid ejected from the second fluid outlet. It is to be understood that a direction of motion of a fluid ejected from a fluid outlet may be defined as the average direction of motion of said fluid. That is, while different portions of said fluid may move in different directions of motion, an overall direction of motion may nevertheless be defined for said fluid as a whole, e.g., by averaging over all said different directions of motion.

For example, the first fluid outlet and the second fluid outlet may be arranged such that, if both the first fluid outlet and the second fluid outlet are operated (simultaneously), fluid ejected from the first fluid outlet collides with fluid ejected from the second fluid outlet at a distance from the treatment area, such that the fluid ejected from the first fluid outlet and the fluid ejected from the second fluid outlet form the fluid covering the third portion. Due to the collision, at least parts of the fluids ejected by the first outlet and the second outlet are deflected, i.e., they change their direction of motion, such that they may eventually reach different parts of the treatment area than they could/would if no collision occurred. For example, the first fluid outlet and the second fluid outlet may be arranged apart such that the fluids ejected therefrom collide above the treatment area. That is, the nozzle assembly may be located/held at a certain height above the treatment area. The first fluid outlet and the second fluid outlets are then arranged such that if both the first fluid outlet and the second fluid outlet are operated (simultaneously), fluid ejected from the first fluid outlet collides with fluid ejected from the second fluid outlet at a distance from the treatment area, i.e., in a region that lies between the nozzle assembly and the treatment area. This is not to be misunderstood as implying that the nozzle assembly may only be used when located/held vertically above the treatment area. Since fluid outlets may be operated using pressure (e.g., pressurized fluids), they may eject the respective fluid in arbitrary directions, in turn allowing the nozzle assembly to provide the fluid used for cooling along any direction, such that the nozzle assembly does precisely not need to be located/held vertically above the treatment area. Irrespective, the skilled person readily understands that hence the arrangement of the fluid outlets may (also) depend on the desired/target distance between the nozzle assembly and the treatment area, which may in turn depend on the desired/target distance between the energy-based medical device with which the nozzle assembly shall be used. This applies in particular if the nozzle assembly is integrated into (a part of) the energy-based medical device.

The concept of the present invention can be readily extended to an arbitrary number of fluid outlets or nozzle assemblies comprising such an arbitrary number of fluid outlets, respectively, e.g., three, four, six, ten or any other number of fluid outlets.

For example, in addition to the first fluid outlet and the second fluid outlet, the nozzle assembly may comprise a third fluid outlet operable individually as well as simultaneously with the first fluid outlet and/or the second fluid outlet. The third fluid outlet may be arranged apart from the first fluid outlet and the second fluid outlet such that the fluid covers a fourth portion of the treatment area if only the third fluid outlet is operated, wherein the fourth portion is not fully contained in the first portion and/or the second portion (and, optionally, vice versa), a fifth portion of the treatment area if both/only the first fluid outlet and the third fluid outlet are operated (simultaneously), wherein the fifth portion is not fully contained in the first portion and/or the fourth portion (and, optionally, vice versa), a sixth portion of the treatment area if both/only the second fluid outlet and the third fluid outlet are operated (simultaneously), wherein the sixth portion is not fully contained in the second portion and/or the fourth portion (and, optionally, vice versa) and/or a seventh portion of the treatment area if (all of/only) the first fluid outlet, the second fluid outlet and the third fluid outlet are operated (simultaneously), wherein the seventh portion is not fully contained in the first portion and/or the second portion and/or the fourth portion (and, optionally, vice versa).

Further, in addition to the first fluid outlet, the second fluid outlet and the third fluid outlet, the nozzle assembly may for example comprise a fourth fluid outlet operable individually as well as simultaneously with the first fluid outlet and/or the second fluid outlet and/or the third fluid outlet. The fourth fluid outlet may be arranged apart from the first fluid outlet, the second fluid outlet and the third fluid outlet such that the fluid covers an eighth portion of the treatment area if only the fourth fluid outlet is operated, wherein the eighth portion is not fully contained in the first portion and/or the second portion and/or the fourth portion (and, optionally, vice versa), a ninth portion of the treatment area if both/only the first fluid outlet and the fourth fluid outlet are operated (simultaneously), wherein the ninth portion is not fully contained in the first portion and/or the eighth portion (and, optionally, vice versa), a tenth portion of the treatment area if both/only the second fluid outlet and the fourth fluid outlet are operated (simultaneously), wherein the tenth portion is not fully contained in the second portion and/or the eighth portion (and, optionally, vice versa), an eleventh portion of the treatment area if both/only the third fluid outlet and the fourth fluid outlet are operated (simultaneously), wherein the eleventh portion is not fully contained in the fourth portion and/or the eighth portion (and, optionally, vice versa), a twelfth portion of the treatment area if (only) the first fluid outlet, the second fluid outlet and the fourth fluid outlet are operated (simultaneously), wherein the twelfth portion is not fully contained in the first portion and/or the second portion and/or the eighth portion (and, optionally, vice versa), a thirteenth portion of the treatment area if (only) the first fluid outlet, the third fluid outlet and the fourth fluid outlet are operated (simultaneously), wherein the thirteenth portion is not fully contained in the first portion and/or the fourth portion and/or the eighth portion (and, optionally, vice versa), a fourteenth portion of the treatment area if (only) the second fluid outlet, the third fluid outlet and the fourth fluid outlet are operated (simultaneously), wherein the fourteenth portion is not fully contained in the second portion and/or the fourth portion and/or the eighth portion (and, optionally, vice versa), and/or a fifteenth portion of the treatment area if (all of/only) the first fluid outlet, the second fluid outlet, the third fluid outlet and the fourth fluid outlet are operated (simultaneously), wherein the fifteenth portion is not fully contained in the first portion and/or the second portion and/or the fourth portion and/or the eighth portion (and, optionally, vice versa).

Generally, by operating two or more fluid outlets simultaneously, (additional) parts of the treatment area may be reached that could not be reached by individual operation of the fluid outlets. On the other hand, generally, by simultaneous operation of (the) two or more fluid outlets parts that can be reached by individual operation may not be reached anymore. In some examples, first and second portions may not overlap, while the third portion at least partly overlaps with each of the first and second portions. In other examples, the first, second and third portions may not mutually overlap at all. The same may apply if more than two fluid outlets are provided. For example, the portions reachable by individual operation of the fluid outlets may not overlap. Those portions reachable by simultaneous operation of two or more fluid outlets may at least partly overlap with the portions reached by individual operation of the respective fluid outlets. Also, portions reachable by simultaneous operation of two or more fluid outlets may at least partly overlap mutually. Additionally or alternatively, portions reachable by simultaneous operation of two or more fluid outlets may not be contained in any combination of the respective other portions reachable by simultaneous operation of two or more fluid outlets. In other examples, all portions may be at least partly or even completely disjoint.

Throughout this disclosure, an overlap (where applicable) may mean an overlap of at least 5%, 10%, 15%, 20%, 25%, 30%, 35%, 40%, 45%, 50%, 55%, 60%, 65%, 70%, 75%, 80%, 85%, 90%, 95% or, in case of full overlap (e.g., where one portion is fully contained in another), 100%. Conversely, additionally or alternatively, an overlap (where applicable) may mean an overlap of at most 5%, 10%, 15%, 20%, 25%, 30%, 35%, 40%, 45%, 50%, 55%, 60%, 65%, 70%, 75%, 80%, 85%, 900%, 950% or, in case of full overlap (e.g., where one portion is fully contained in another), 100%. It is noted that these percentages may refer to either of the respective overlapping portions. As a consequence, the percentages may differ depending on which portion they refer to, even though they label the same actual overlap. For example, where one of two overlapping portions is twice as large as the other, the latter being fully contained in the former, the overlap is 100% when referring to the latter, but only 50% when referring to the former.

Generally, while portions covered by fluid upon operation of a respective single fluid outlet may in principle be mutually identical and/or contained within each other, portions covered by fluid upon (simultaneous) operation of a plurality of fluid outlets may not be fully contained in the portions covered by fluid upon individual operation of the fluid outlets of said plurality of fluid outlets: By operating (at least) two fluid outlets simultaneously, parts of the treatment area may be covered with fluid that would not be covered with fluid by operating the (at least) two fluid outlets individually.

In some embodiments, the fluid used for cooling the treatment area (i.e., the fluid covering the different portions of the treatment area) may be an atomized liquid spray, e.g., a mixture of a liquid and a gas. The gas may be air, but may also be any other suitable gas or gas mixture which is not inflammable or harmful, e.g., to humans. In what follows, the word "air" will be used from time to time to represent a gas in general (not limited only to air). An example of another suitable gas besides air is nitrogen. Similarly, the liquid may be water, but may be also any other suitable liquid, liquid mixture or solution that is not inflammable or harmful to, e.g., humans. Atomized liquid sprays have generally been found to provide for good cooling, without entailing the hazards associated with, e.g., cryogen sprays and/or refrigerants used therein.

In some embodiments, at least one of the first fluid outlet and the second fluid outlet may be configured to eject the atomized liquid spray. That is, the respective fluid outlet may be an internal-mixing outlet, making the nozzle assembly, at least partially, an internal-mixing nozzle assembly. Notably, in such embodiments, the respective fluid outlet is configured to immediately eject the same type of fluid used for cooling the treatment area, i.e., the type of fluid covering the different portions thereof, potentially enhancing targeted application of the atomized liquid spray. This is not mandatory, though, as will become apparent in the following. For example, the first fluid outlet and/or the second fluid outlet may be configured to only eject one or more components of the fluid used for cooling the treatment area.

For example, at least one of the first fluid outlet and the second fluid outlet may be configured to eject gas such that the gas impinges upon a liquid to generate the atomized liquid spray. (It is noted that this may be implemented not only as any alternative, but in addition to the above: For example, the first fluid outlet may be configured to eject atomized liquid spray, whereas the second fluid outlet may be configured to eject gas such that the gas impinges upon a liquid to generate atomized liquid spray, or vice versa.) Due to the collision of the gas and the liquid, the liquid is atomized into small liquid droplets which form the spray. That is, the respective outlet may be an external-mixing outlet, making the nozzle assembly, at least partially, an external-mixing nozzle assembly. Therein, the gas stream(s) ejected from the respective fluid outlet(s) (which has/each have a certain direction of motion when being ejected from the respective fluid outlet) may take along the liquid, so that the generated atomized liquid spray has the direction of motion of the (combined, e.g., aggregate) gas stream(s). (It is noted that a combined, e.g., aggregate gas stream likewise has a certain direction of motion, e.g., defined by the average direction of motion of the combined, e.g., aggregate gas stream.) This way, the direction of motion of the atomized liquid spray can be controlled by controlling the direction(s) of motion of the (combined, e.g., aggregate) gas stream(s). Consequently, the region on the tissue surface (e.g., the portion(s) of the treatment area) which the fluid is applied to is (also) determined by the direction(s) of motion of the emitted/ejected gas stream(s). It is further noted that the geometry of the respective fluid outlet(s), in particular its/their orientation within three-dimensional space, determines the direction of the (combined, e.g., aggregate) gas stream(s) which is/are ejected from the fluid outlet(s). This enables a precise control of the location on the tissue surface to which the atomized liquid spray is applied.

In particular, the at least one of the first fluid outlet and the second fluid outlet may be configured to eject the gas in a pulsed manner, preferably at a pulse period of 10 ms to 5000 ms, more preferably at a pulse period of 100 ms to 2000 ms. Therein, the pulse period is defined as the temporal separation between two successive pulses. It should be noted that such pulsed application of the atomized liquid spray to the tissue, resulting from at least one of the first fluid outlet and the second fluid outlet being configured to eject the gas in a pulsed manner, has the advantage that, in between two successive pulses, evaporation of droplets can take place on the tissue surface, thus avoiding (constantly) wet tissue/skin. Further, especially using the above pulse period ranges, the nozzle assembly is operated in such a way as to achieve a fine "micro-pulsed" liquid spray with optimal liquid content, droplet size and velocity, which together enable quick evaporation of the droplets and thus quick cooling of the tissue surface.

Additionally or alternatively, the at least one of the first fluid outlet and the second fluid outlet may be configured to eject the gas at a pressure of 0.1 bar to 20 bar, preferably at a pressure of 1 bar to 10 bar. Such levels for the gas pressure may allow the (combined, e.g., aggregate) gas stream(s) ejected from the respective outlet(s) to have enough force to take along the liquid (provided, e.g., in the form of one or more liquid drops and/or droplets), so that the direction of motion of the generated atomized liquid spray essentially follows (and/or is essentially determined by) the direction of motion of the (combined, e.g., aggregate) gas stream(s) as already outlined above. Moreover, the first fluid outlet and the second fluid outlet may be configured to eject gas at different pressures, either within or beyond the ranges specified above. This may allow to further finetune the direction of motion of, i.e., steer, the (combined, e.g., aggregate) gas stream(s).

As is clear from the above, and as already hinted at earlier, the first fluid outlet and/or the second fluid outlet may be configured to immediately eject the fluid used for cooling the treatment area, i.e., the fluid covering the respective portions thereof. However, they do not have to. For example, the first fluid outlet and/or the second fluid outlet may be configured to (each) eject a fluid different from that used for cooling the treatment area, i.e., a fluid that is different from the fluid covering the respective portions of the treatment area. For example, the first fluid outlet and/or the second fluid outlet may be configured to (each) only eject one or more components of the fluid used for cooling the treatment area, i.e., the fluid covering the respective portions of the treatment area (which may, e.g., be an atomized liquid spray). Moreover, therein, the first fluid outlet and the second fluid outlet may be configured to eject the same or different fluids.

Furthermore, the nozzle assembly may comprise a liquid outlet configured to eject the liquid. Thus, the liquid spray is generated by using separate outlets for the liquid and the gas. Accordingly, the atomized liquid spray is, at least partially, generated outside the nozzle assembly, when the gas stream(s) ejected from the fluid outlet(s) impinge(s) on the liquid ejected from the liquid outlet. The ratio of the liquid to the gas in the atomized liquid spray is important for achieving the optimal liquid content in the atomized liquid spray. The ratio of the liquid to the gas in the atomized liquid spray may be regulated by controlling the liquid flow from the liquid outlet and/or the gas stream(s) from the fluid outlet(s). Already therefore, it is advantageous to have a liquid outlet in the nozzle assembly, facilitating control of the ejection of the liquid and hence control of, e.g., the liquid content in the atomized liquid spray.

In some embodiments, the liquid outlet may be configured to eject the liquid in the form of a liquid stream. Ejecting the liquid in the form of a liquid stream may result in a higher liquid content in the atomized liquid spray. Moreover, if the liquid is ejected in the form of a liquid stream, this may influence the direction of motion of the generated atomized liquid spray. Put differently, also ejecting the liquid (and not only the gas) in the form of a stream may allow to (further) finetune the direction of motion of the generated atomized liquid spray: Rather than relying only on the (combined, e.g., aggregate) direction(s) of motion of the gas stream(s) ejected from the fluid outlet(s), one may additionally rely on the direction of motion of the liquid ejected from the liquid outlet to not only form, but also steer the generated atomized liquid spray, enhancing overall control over the generated atomized liquid spray.

In other embodiments, the liquid outlet may be configured to eject the liquid in the form of one or more drops, or droplets, dangling from the liquid outlet. Said liquid drop may be carried away by the (combined, e.g., aggregate) gas stream(s) in the form of a mist, i.e., an atomized liquid spray, wherein the spatial distribution of the mist/atomized liquid spray follows approximately the spatial distribution of the (combined, e.g., aggregate) gas stream(s). Typically, the atomized liquid spray has approximately the form of a cone which extends from the respective fluid outlet(s) to the surface to be cooled. That is, ejecting the liquid in the form of a drop dangling from the liquid outlet facilitates control of the resulting atomized liquid spray in that its direction of motion is (solely) defined by the direction(s) of motion of the (combined, e.g., aggregate) gas stream(s) ejected by the fluid outlet(s).

In particular, the liquid outlet may eject the liquid in the form of a drop dangling from the liquid outlet if it is configured to eject the liquid at a rate of 0.001 ml/min to 30 ml/min, preferably 0.2 ml/min to 4 ml/min. Additionally, using liquid flows in the specified range may be beneficial for the effective cooling of the tissue surface area by means of the fast evaporation of liquid droplets of the spray. On the one hand, such liquid flows ensure that a sufficient number of liquid droplets are deposited onto the tissue area, in order to provide a cooling effect. On the other hand, when using such liquid flows, the number of liquid droplets is not so high that a liquid film is formed. As noted above, such a liquid film is undesirable since it would effectively reduce the liquid evaporation rate and would also cause an uncomfortable and undesirable over-wetting of the patient.

Additionally or alternatively, the liquid outlet may be configured to eject the liquid with a low pressure in the range from 0.1 to 0.5 bar. The low pressure of the liquid (and a correspondingly low velocity of the liquid particles) may add to the effect that the (combined, e.g., aggregate) gas stream(s) from the fluid outlet(s) determine(s) the direction of motion of the generated atomized liquid spray. Besides, a low pressure of the liquid helps in avoiding a dripping of the liquid when the nozzle assembly, or at least the liquid outlet, is turned off.

Generally, the liquid outlet may have an orifice, wherein this orifice has a diameter from 0.1 to 1 mm, preferably from 0.3 to 0.5 mm. Especially the above-specified range for the pressure and the above-specified range for the flow of the liquid are compatible with an orifice which has a rather large diameter. Thus, the problems when using orifices with a small diameter (i.e., in the order of several micrometers) are avoided. In particular, orifices with a small diameter clog very quickly, i.e., temporarily by small gas bubbles which are always present in flowing liquids, and, in the long term, by sediments and impurities within the liquid.

In some embodiments, the liquid outlet may be configured to eject the liquid in a pulsed manner, e.g., using a pumping means. Such pulsed operation of the liquid outlet leads to a good control of the liquid flow, as the frequency of the pulses can be varied. In some embodiments, the liquid outlet and/or pumping means may operate with a frequency from 0.1 to 1 kHz, preferably from 0.5 to 50 Hz. Especially for achieving the above-specified small liquid flows, a positive displacement pump can be used. Positive displacement pumps draw the fluid into a compartment at the inlet end and move the fluid to the outlet for discharge. A positive displacement pump moves the liquid at the same speed regardless of the pressure on the inlet end. Positive displacement pumps can be classified according to the method which moves the liquid, namely a rotary or an oscillating (reciprocating) method. However, it is noted that rotary positive displacement pumps are relatively complicated. Moreover, an oscillating positive displacement pump has the advantage that it naturally lends itself to a pulsed operation. Thus, an oscillating positive displacement pump is a preferred embodiment for the pumping means. A diaphragm pump, which is a sub-class of oscillating positive displacement pumps, is an even more preferred embodiment for the pumping means.

Generally, the liquid may comprise one or more of the following additives: a solution which enhances the evaporation rate, a solution which conditions the skin, a solution for aromatherapy, and a disinfecting solution. These additives may enhance the performance of the nozzle assembly in terms of cooling effect, user experience and/or safety. Other additives can be mixed into the spray as well, in order to support moisturizing, a faster healing, disinfection, pain reduction, or the creation of a more pleasant aroma. More generally, any of the above substances may be added to the fluid, to the gas or to both, which may most effectively combat the undesirable odor which, for example, results from laser ablation of human tissues. In this context, it is noted once again that the liquid may be water, but may also be any other suitable liquid or liquid mixture or solution which is not inflammable or harmful to patients. For example, a water-alcohol solution may be used, provided that the alcohol concentration does not exceed the concentration of about 50% at which point the solution becomes inflammable, especially under laser irradiation. Adding rapidly evaporating liquids such as alcohol to the liquid speeds up the evaporation of the liquid droplets of the atomized liquid spray, and hence enhances the cooling rate.

In some embodiments, the size of the droplets of the atomized liquid spray which is generated by the nozzle assembly may be in the range from 5 to 200 micrometers, more preferably from 10 to 100 micrometers. It is noted that the droplets need to be small enough to evaporate when being in contact with the treated skin so that a fusing of the droplets and the formation of a liquid film on the skin surface is avoided. As already mentioned, such a liquid film lowers the heat transfer rate from the skin to the liquid medium. On the other hand, the droplets need to be sufficiently large for sticking to the skin surface and for enabling the heat transfer from the epidermis to the cooling medium. It is also noted that the size of the droplets is influenced by the size of the orifice of the liquid outlet.

In certain embodiments, the nozzle assembly comprises (at least) one liquid outlet in combination with a plurality of fluid outlets configured to eject gas such that the gas impinges upon a liquid ejected from the liquid outlet to generate the atomized liquid spray. For example, the liquid outlet may be located between the first fluid outlet and the second fluid outlet, preferably on a straight line extending from the first fluid outlet to the second fluid outlet. More generally, the plurality of fluid outlets may surround the (at least one) liquid outlet, e.g., in a symmetric or an asymmetric manner.

By using a nozzle assembly having a plurality of fluid outlets (configured to eject gas) near one liquid outlet, the generated atomized liquid spray can be directed to different regions on the tissue surface (without moving the nozzle assembly, or the apparatus for cooling tissues, in which the nozzle assembly may be employed, itself). Namely, each fluid outlet may have a different direction into which the gas is ejected. Since the gas takes along the liquid when the atomized liquid spray is generated, the different directions into which the fluid outlets point correspond to different regions on the tissue surface where the spray is applied. A plurality of fluid outlets is particularly helpful if the atomized liquid spray shall cover a relatively large tissue surface (e.g., a large area of the skin), since switching between the various fluid outlets is generally faster than changing the orientation of a single fluid outlet or the nozzle assembly as a whole.

Moreover, if two or more gas streams ejected from respective fluid outlets (each one accordingly having a different direction of motion) hit the liquid at the same time, the direction of the atomized liquid spray generated thereby is roughly parallel to the direction of the combined, e.g., aggregate, momentum of the gas pulses. Consequently, it is possible to spray areas that remain unsprayed when using individual gas streams. Furthermore, when such combined, e.g., aggregate gas streams are used in combination (e.g., in temporal sequence) with individual gas streams, it is possible to spray any area on a tissue surface (e.g., under the nozzle assembly) and thus modify the shape of the sprayed area to desired form. This allows optimization of the cooling efficiency and minimization in the use of cooling power, as the areas of skin that are not significantly heated during the delivery of energy can be bypassed.

In some embodiments, each one of the fluid outlets has a corresponding delivery means. This is helpful for the independent operation of each fluid outlet, i.e., the operation of one fluid outlet should not interfere with, or depend on, the operation of another fluid outlet. Thus, preferably, the gas flow from each one of the fluid outlets can be controlled independently of that from the other fluid outlet(s).

In a second aspect, the present invention relates to a method of cooling a treatment area with a fluid using a nozzle assembly as discussed above. Such method comprises operating at least one of the first fluid outlet and the second fluid outlet individually as well as operating the first fluid outlet and the second fluid outlet simultaneously. As described at length above, such simultaneous operation of the first fluid outlet and the second fluid outlet allows to provide fluid to parts of the treatment area that would not be provided with fluid if the first fluid outlet and the second fluid outlet were exclusively operated individually. Conversely, operating the first fluid outlet and the second fluid outlet both individually as well as simultaneously allows to provide fluid to large areas, e.g., in a scanning manner.

In particular, such method and/or the fluid nozzle according to the present invention may be used to cool a treatment area that is treated by an energy-based medical device such as a laser. The method and/or the fluid nozzle according to the present invention may be suitable to avoid overheating. For example, the method and/or the fluid nozzle according to the present invention may keep the temperature of the treatment area below 50° C., preferably below 42° C., more preferably below 37° C., most preferably below 33° C. Therein, the method and/or the fluid nozzle according to the present invention may be used to (essentially evenly) cool large treatment areas of a size between 5 cm$^2$ and 10000 cm$^2$, preferably between 10 cm$^2$ and 5000 cm$^2$, more preferably between 25 cm$^2$ and 4000 cm$^2$, most preferably between 50 cm$^2$ and 500 cm$^2$.

To this end, the nozzle assembly can be integrated into the handpiece of a laser system, e.g., as part of an apparatus for cooling. This way, the fluid used for cooling by the nozzle assembly can be easily applied at or near the treatment area which is irradiated by the laser pulses, wherein these laser pulses are emitted from the handpiece of the laser system. Similar considerations apply to other energy-based medical devices.

Preferably, a device which ejects a jet of cold air is additionally mounted on the handpiece of the laser piece. The cold air which is ejected from this device can provide an additional cooling effect for the treated tissue (in addition to the cooling by means of the fluid). In particular, as discussed in more detail below, there is a synergistic effect between the cooling by means of cold air and the cooling by means of the fluid, since the achieved cooling effect (measured as the drop of temperature of the cooled tissue) when both the fluid and the cold air are applied is greater than the sum of the cooling effects for the fluid and the cold air.

Preferably, the temperature of the cold air is in the range from −40° C. to 0° C., more preferably from −35° C. to −20° C.

According to another aspect, the nozzle assembly is mounted on the scanning device of a laser scanner, e.g., as part of an apparatus for cooling. Such laser scanners are often used for the treatment of large areas, e.g. the skin of a human or animal.

Further preferred embodiments are described in the appended dependent claims.

It is noted that any combination of features that have been described above as belonging to certain embodiments/aspects of the present invention is also an embodiment of the present invention, provided such a feature combination is feasible, i.e., does not lead to any contradictions.

DETAILED DESCRIPTION OF PREFERRED EMBODIMENTS

Figure 2:
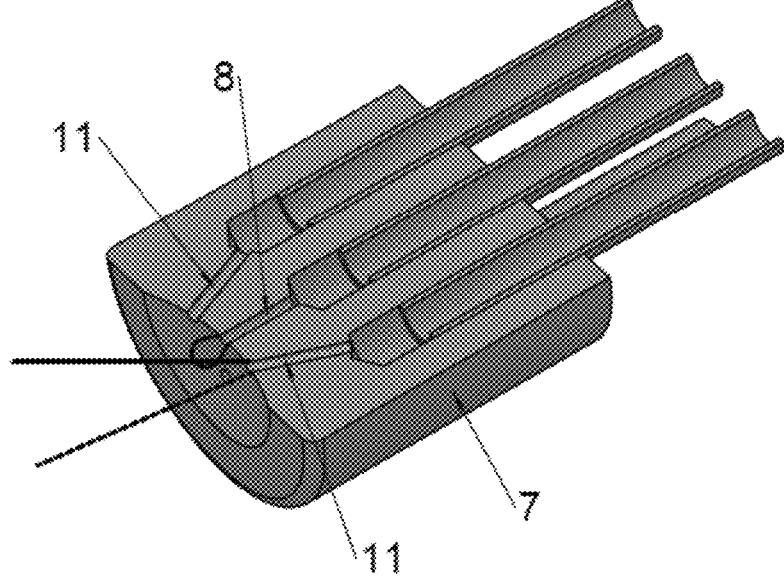
Figure 3:
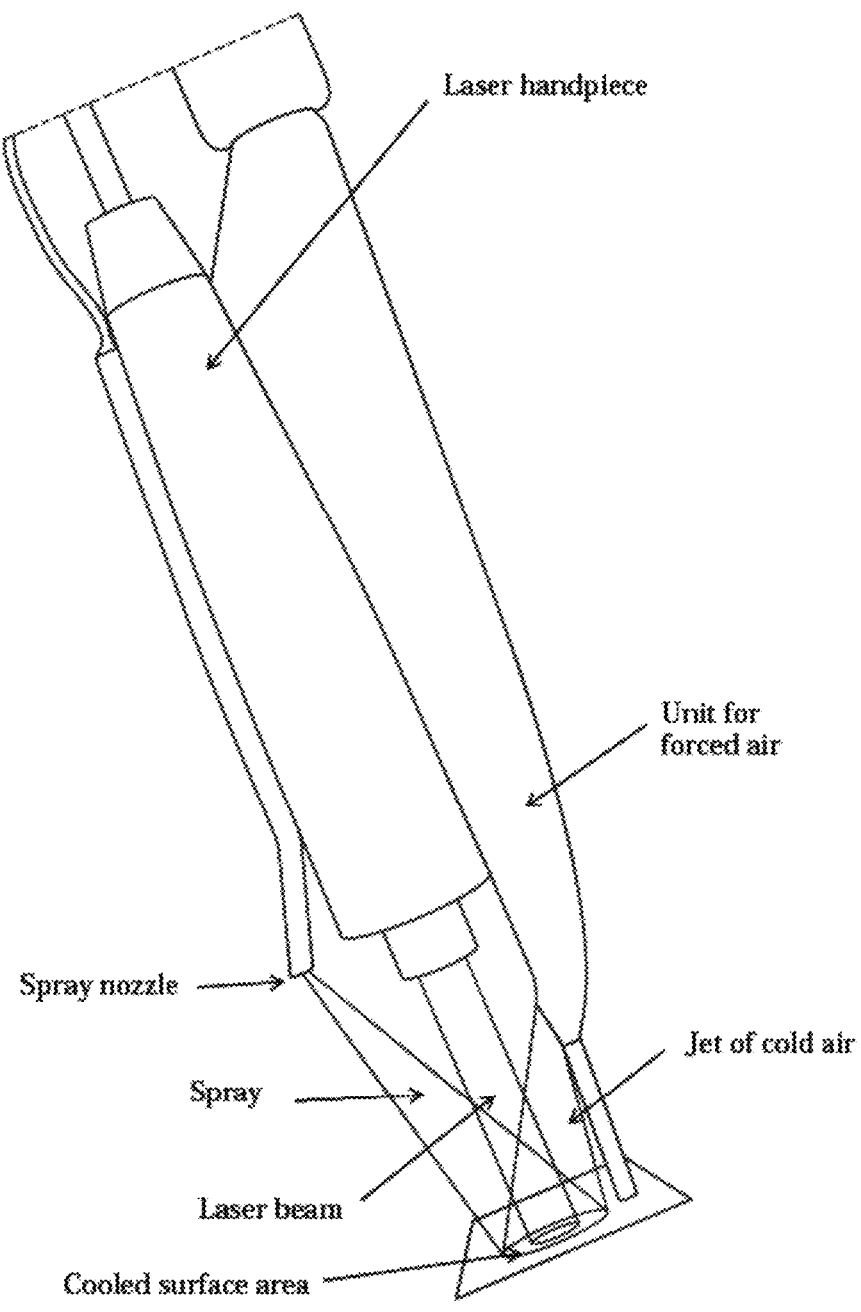
Figure 4:
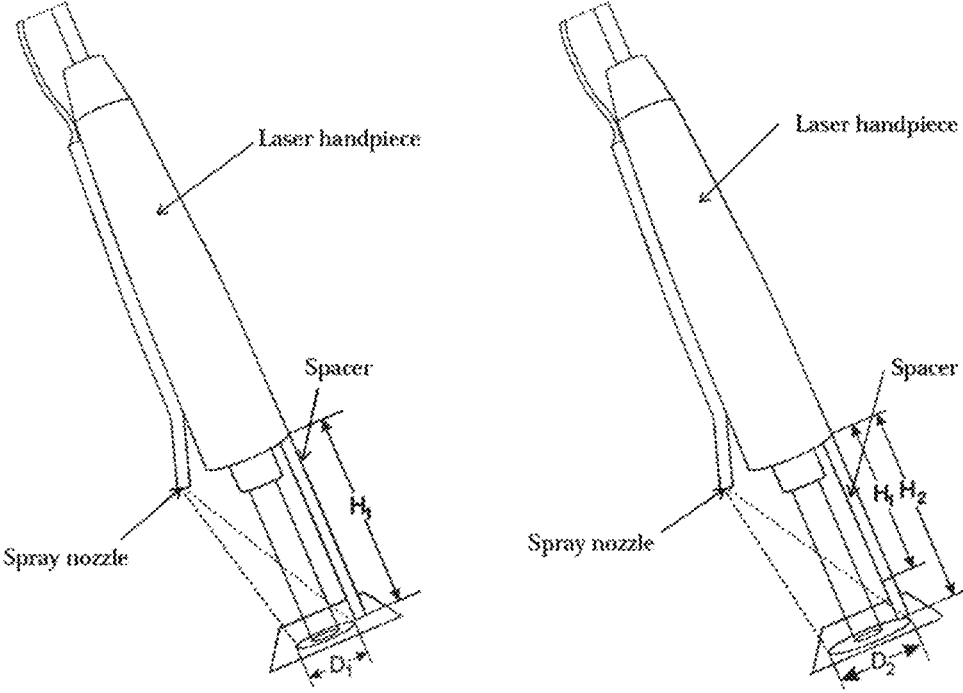
Figure 5:
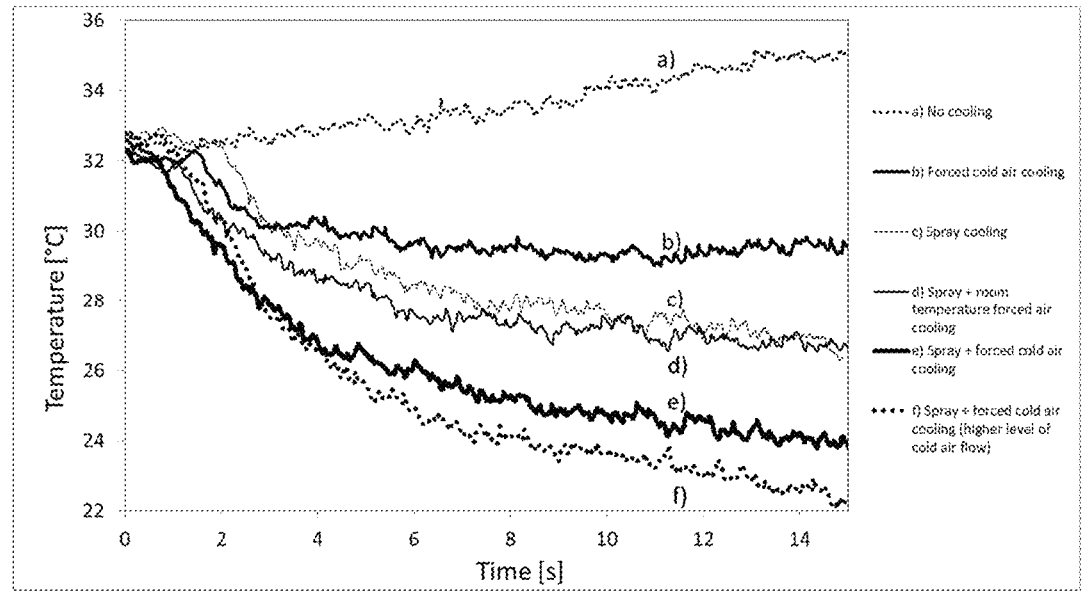
Figure 6:
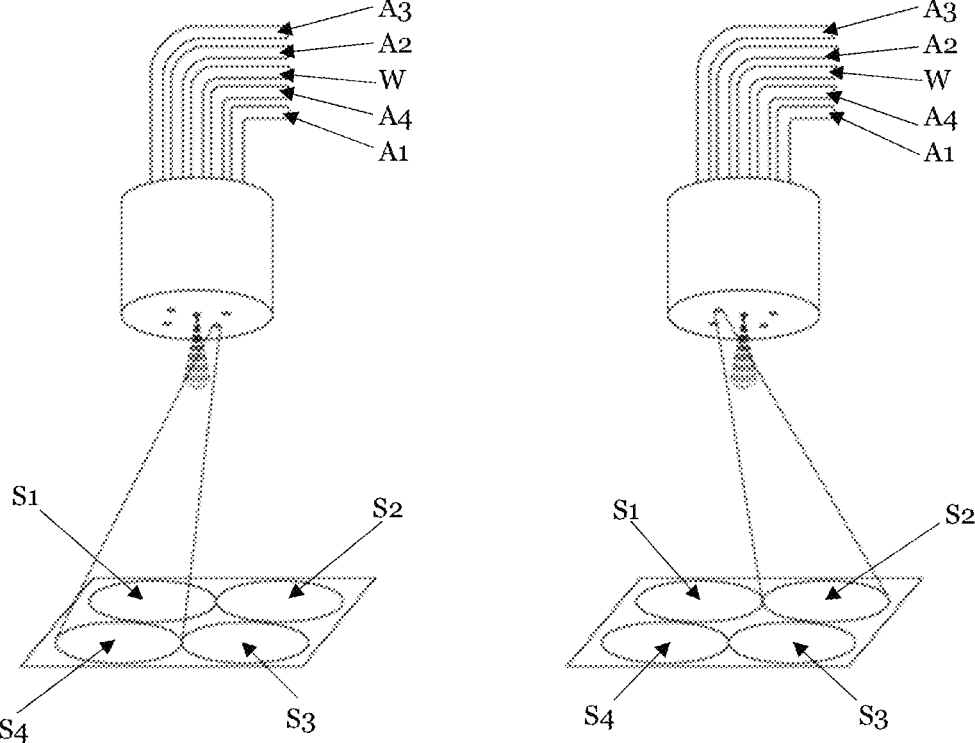
Figure 7:
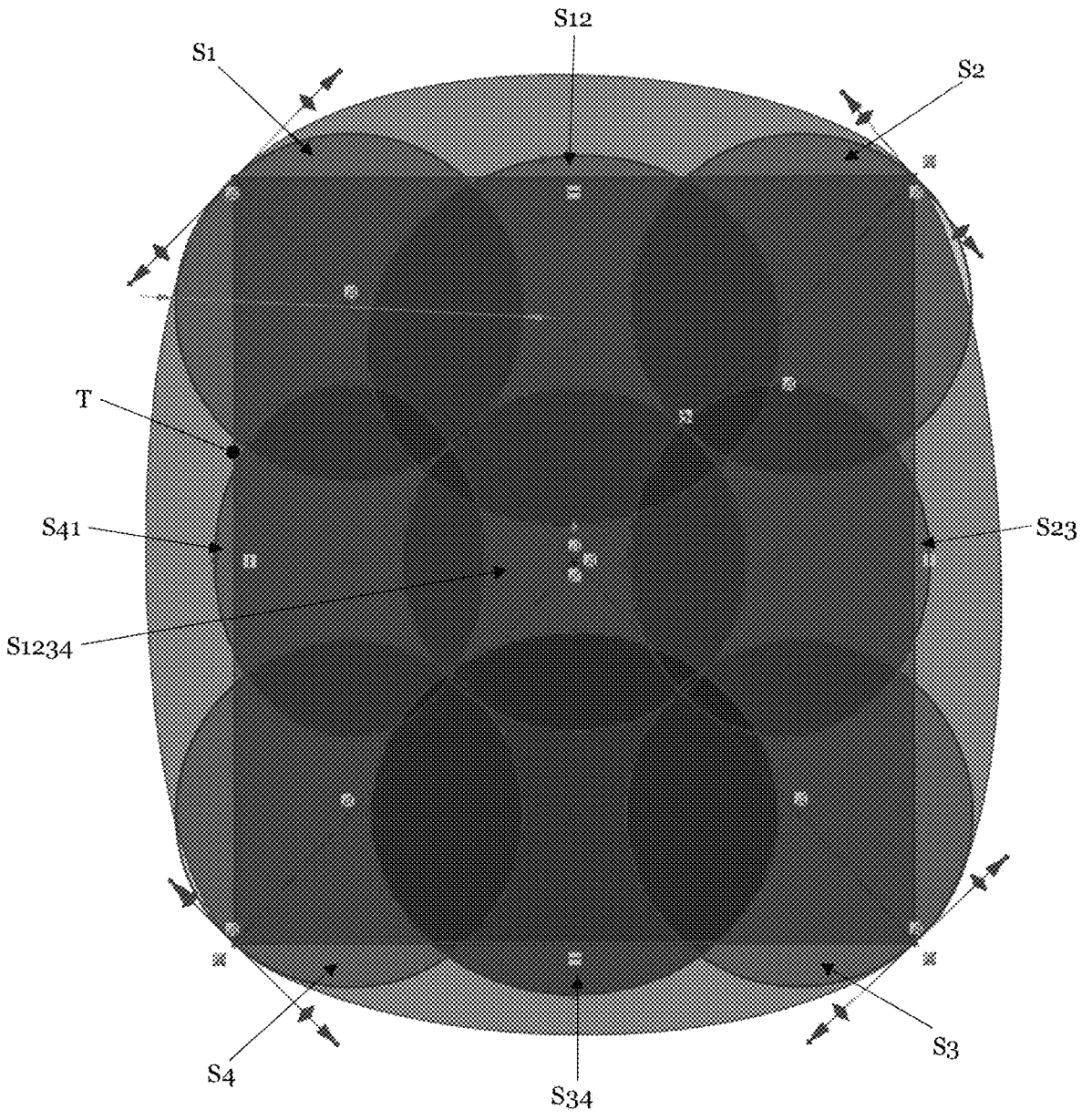

Some of the embodiments of the invention will be explained in the following with the aid of the Figures in more detail. It is shown in:

FIG. 1: an apparatus for cooling tissues using a nozzle assembly according to the present invention;

FIG. 2: a nozzle assembly which comprises one liquid outlet and four fluid outlets configured to eject gas;

FIG. 3: a laser handpiece to which an apparatus for cooling tissues using a nozzle assembly according to the present invention is attached;

FIG. 4: a schematic view of how the treatment area to which the fluid for cooling is applied can be varied by changing the distance between the nozzle assembly and the tissue surface;

FIG. 5: a comparison of skin surface temperature as measured under laser irradiation for six different cooling methods;

FIG. 6: a schematic view of a nozzle assembly which combines a single liquid outlet with four fluid outlets configured to eject gas;

FIG. 7: a schematic view of different portions of a treatment area that the fluid for cooling may cover depending on which fluid outlets of the nozzle assembly of FIG. 6 are operated.

FIG. 1 illustrates an apparatus 100 for cooling tissues with a fluid which comprises a liquid reservoir 1, a pumping means 2, a gas reservoir 10, a gas compressor 3, gas valves 9 and a gas pressure regulator. Apparatus 100 further comprises delivery means 5 for the liquid and delivery means 6, 6' for the gas, wherein these delivery means combine within a nozzle assembly 7.

Delivery means 5 having the form of a tube delivers the liquid from liquid reservoir 1 to nozzle assembly 7, wherein the flow of the liquid is regulated by pumping means 2. In the embodiment of FIG. 1, pumping means 2 is a low-pressure pump (for example, a diaphragm pump). The low-pressure pump works in a pulsed mode with frequencies in the range from 0.1 to 1 kHz, preferably from 0.5 to 50 Hz.

Delivery means 6, 6' for the gas also has the form of a tube and delivers gas from gas reservoir 10 through gas compressor 3 to nozzle assembly 7, wherein gas compressor 3 is used for regulating the gas pressure. In the apparatus of FIG. 1, gas pressure is in the range from 1 to 10 bar.

It is noted that FIG. 1 shows a plurality of gas valves 9 which correspond to a plurality of fluid outlets 11 within nozzle assembly 7, each fluid outlet 11 configured to eject gas. This way, by opening and closing various gas valves 9, it can be controlled which one or more fluid outlets 11 eject gas at a certain moment. Further, by controlling gas valves 9 and thereby activating/operating specific fluid outlets 11, the direction of movement of the fluid for cooling the treatment area, specifically the atomized liquid spray (in the following simply "spray") which is generated by/ejected from nozzle assembly 7, can be determined. Besides, by modifying the pattern, length and momentum of the gas streams ejected from respective fluid outlets 11 using gas valves 9, a desired shape of the sprayed area can be achieved.

It is noted that, according to FIG. 1, pumping means 2, gas compressor 3 and gas valves 9 are connected to spray controller 4. Thus, spray controller 4 can control the amounts of liquid and gas which are delivered to nozzle assembly 7 as well as the pressures under which liquid and gas are delivered. As such, spray controller 4 also controls which of the fluid outlets 11 is operated. In particular, spray controller may operate each of the fluid outlets 11 individually. But it may also operate two or more fluid outlets 11 simultaneously.

Spray controller 4 itself is connected to a computer control means 12 of an energy-based device (not shown) so that synchronization of the pulsed spray operation with the pulses of the energy-based device may be enabled. In some embodiments, computer control means 12 may assume at least some (e.g., one or more) of the functions of spray controller 4. Vice versa, in some embodiments, spray controller 4 may assume at least some (e.g., one or more) of the functions of computer control means 12. In some embodiments, spray controller 4 and computer control means 12 may be the same entity, i.e., there may be only either a spray controller such as spray controller 4 or a computer control means such as computer control means 12.

It is further noted that the amount of liquid in the spray, the liquid/gas ratio and/or the droplet size are important factors for achieving an optimal evaporation cooling for the epidermal surface. Here, the amount of liquid in the spray may be regulated, e.g., by a pulsed operation of pumping means 2 or by regulating the pressure in liquid reservoir 1. In particular, pumping frequencies between 1 and 20 Hz have been used for obtaining a suitable liquid content for the spray, wherein the liquid flow rates are between 0.001 and 30 ml/min, preferably between 0.2 and 4 ml/min.

The gas/liquid ratio can be regulated through the combined regulation of pumping means 2 and the gas pressure from gas reservoir 10. The gas pressure for achieving a suitable gas/liquid ratio of the spray is in the range from 0.1 to 20 bar, preferably from 1 to 10 bar. The corresponding liquid flow density of the spray is in the range from 0.001 to 2 $ml/(min \times cm^2)$, preferably in the range from 0.002 to 0.5 $ml/(min \times cm^2)$. This ensures that, on the one hand, there is a sufficient number of sufficiently small liquid droplets being deposited onto the surface area to be cooled and, on the other hand, the number of liquid droplets is not too high, thus avoiding the formation of a liquid film (which would effectively reduce the liquid evaporation rate and cause an uncomfortable and undesirable over-wetting of the patient, of the bed and of the surrounding).

As noted above, liquid flows for typical treatment areas and cooling times are in the range of 0.001 to 30 ml/min. These are very small liquid flows which are technically very challenging to achieve in a reliable manner. In particular, a positive displacement pump can be used within the apparatus for cooling according to FIG. 1. Positive displacement pumps draw the fluid into a compartment at the inlet of the pump and move the fluid to the outlet for discharge, wherein the liquid has the same speed regardless of the pressure at the inlet. Such positive displacement pumps can be classified according to the method which is used for moving the liquid, namely a rotary or an oscillating (reciprocating) method. However, rotary positive displacement pumps are relatively complicated. Moreover, an oscillating positive displacement pump has the advantage that it naturally lends itself to a pulsed operation. Thus, an oscillating positive displacement pump, in particular a diaphragm pump, is used as pumping means 2 in the apparatus for cooling according to FIG. 1. By operating these low-pressure pumps in pulses, the level of the liquid flow can be precisely regulated.

Due to the low liquid flow and the low liquid pressure, relatively large orifices of the liquid outlet 8 of nozzle assembly 7 can be used. In particular, the diameter of the orifice can be in the range from 0.1 to 1.0 mm.

FIG. 2 shows a view of nozzle assembly 7, wherein the nozzle assembly comprises one liquid outlet 8 and four fluid outlets 11, all of them configured to eject gas (two of them are shown sliced). The liquid and fluid outlets are arranged in such a way that the resulting spray cloud/mist can be directed towards different regions of the treatment area as will be explained in more detail below with reference to FIGS. 6 and 7. When using the nozzle assembly according to FIG. 2, the liquid stream from liquid outlet 8 and the gas stream(s) from one or more of fluid outlets 11 are mixed externally in order to generate an atomized liquid spray.

FIG. 3 illustrates a laser handpiece to which an apparatus for cooling tissues using a nozzle assembly according to the present invention (labelled "spray nozzle" therein) is attached. It is noted that the corresponding laser system comprises a laser system body, a laser delivery means (e.g., an articulated arm or an optical fiber), and the handpiece (as shown in FIG. 3), wherein the handpiece is connected to the distal end of the laser delivery means. The optics and configuration of the handpiece determine the shape and size of the laser-irradiated area. Both the pumping means and the gas pressure regulator/gas compressor of the apparatus for cooling tissues are connected to the computer control means of the laser system. This way, a synchronization of the pulsed spray operation with the emitted laser pulses is possible.

As can be seen in FIG. 3, a spray is ejected from the nozzle assembly, wherein the transversal cross-section of the ejected spray successively widens so that the spray jet has the form of a cone. It is noted that the spray is directed to the treatment area on the tissue surface, i.e., the area on the tissue surface to which the spray is directed essentially corresponds to the spot size of the laser beam which is emitted from the handpiece. Thus, if spray and laser pulses are synchronized, the spray cooling of the tissue can take place simultaneously with the laser treatment of the tissue.

The cone angle of the generated spray can for example be up to 20° (see FIG. 3). The cone angle and the distance between nozzle assembly and treatment area determine the surface area where a spray pulse is applied (this surface area is simultaneously cooled by the spray). For example, if a distance H from the gas nozzle to the surface to be cooled is H=20 cm, the diameter $D_1$ of the area which is cooled is approximately equal to $D_1$=7 cm. In some examples, the area which is cooled is cooled homogenously across the entire diameter $D_1$. In other examples, the area which is cooled is cooled homogenously only across a portion of the diameter $D_1$, e.g., across a diameter $D_0$. In some examples, the diameter $D_0$ that corresponds to a central part which is relatively homogenously cooled is $D_9 \approx 3$ cm.

The size of the area to which the spray is applied can be adjusted to the size of the treatment area by adjusting the height H as shown in FIG. 4. In particular, FIG. 4 shows that the area on the tissue surface to which the spray is applied increases if the height $H_1$ is increased to $H_2$. More generally, the area to which the spray is applied can (also) be modified by changing the height and/or the angle of the nozzle assembly (labelled "spray nozzle" in FIG. 4) relative to the tissue. Of course, this form of adjustment of the sprayed area requires a movement of the nozzle assembly (together with the apparatus for cooling tissues), which is generally cumbersome, imprecise and slow. Hence, it may effectively only be used for a coarse adjustment/modification of the sprayed area, if at all: Generally, the distance between the treatment area and the nozzle assembly, especially when used in conjunction with an energy-based (medical) device such as just described, may not be arbitrarily chosen (e.g., such as to adjust which parts/portions of the treatment area shall be cooled). Rather, the distance between the treatment area and the nozzle assembly may be limited, e.g., by the working distance required by the energy-based (medical) device. It is hence important to notice that some or even all of the advantages of the present invention as described herein may not simply be realized by varying the distance between the treatment area and the nozzle assembly. Rather, the present invention generally requires a particular arrangement (e.g., including a particular orientation) of the fluid outlets to achieve the desirable effects described herein. It is to be understood that, therein, said arrangement (e.g., orientation) of the fluid outlets may depend on the distance between the treatment area and the nozzle assembly, which may in turn depend on the working distance of an energy-based (medical) device in conjunction with which the nozzle assembly is to be used.

In some embodiments of the invention, the height H of the nozzle assembly above the treatment area is controlled by a spacer of a certain length, wherein the spacer can be mounted to the laser handpiece and wherein the length of the spacer can be changed by operating a mechanism. As can be seen in FIG. 4, a spacer of a certain length contacts the skin surface (in the surroundings of the treatment area) and hence keeps the distance between the nozzle and the tissue surface constant (i.e., the value H is kept constant). In the two parts of FIG. 4, the length of the spacer is increased from $H_1$ to $H_2$ so that the height of the nozzle above the treatment area is increased, as well. In yet another embodiment of the invention, the angle of the nozzle assembly relative to the tissue can be regulated by adjusting a joint-type element between the nozzle assembly and the body of the laser handpiece.

FIG. 3 also shows a unit which ejects a stream of cold air, wherein this unit is also attached to the laser handpiece. The stream of cold air is directed to the treatment area and thus has a cooling effect for the treatment area (in addition to the atomized liquid spray from the nozzle assembly). It is noted that, in FIG. 3, a spacer is mounted to the unit for cold air.

In order to quantify this additional cooling effect, FIG. 5 shows a comparison of the skin surface temperature as measured under laser irradiation, displaying the effect of different cooling methods as follows:

line a: no cooling;
  line b: forced cold air cooling using a commercial Cryo 6 device (manufactured by Zimmer);
  line c: micro-pulsed spray cooling as described above;
  line d: micro-pulsed spray cooling as described above combined with forced air cooling (air at room temperature); and
  lines e, f: micro-pulsed spray cooling as described above combined with forced air cooling (cold air from Cryo 6 device) for two different levels of cold air flow.

As can be seen from FIG. 5, micro-pulsed spray cooling as described above is significantly faster (cf. line c) than the commonly used forced cold air cooling (cf. line b). We have also found out that the cooling rate of the micro-pulsed spray cooling can be additionally increased by directing an additional forced cold air flow to the treated area (cf. lines e and f). On the other hand, an additional forced air flow at room temperature does not significantly contribute to the cooling rate (cf. line d).

Sometimes, large areas of tissue must be irradiated, for example during a hair removal procedure where a handpiece with a large spot size of the laser beam or a canning device is used. Then, the application area of the spray may be too small, especially where homogenous cooling is desired, but where only a portion of the area that is cooled is cooled homogenously. For example, the diameter $D_1$ of the area which is cooled may be approximately equal to $D_1 \approx 7$ cm, which may already be less than the diameter of the laser spot. Meanwhile, the diameter $D_0$ that corresponds to a central part which is relatively homogenously cooled may be only $D_0 \approx 3$ cm, exacerbating the problem. Besides, it may be desirable that the laser beam is moved over a treatment area such that pre-cooling is performed, i.e., a tissue area is cooled before being irradiated. Similarly, it may be advantageous to post-cool a tissue area that has been irradiated. Alternatively, it may be advantageous to be able to pre-cool, cool and post-cool the treated tissue when moving the laser beam across the treatment area.

In such cases, a "scanning micro-pulse spray apparatus" according to the present invention can be used where at least one liquid outlet is combined with a multiplicity of fluid outlets, wherein each fluid outlet is configured to eject gas and is directed to a different region, or portion, of the tissue/treatment area. By operating the multiplicity of fluid outlets individually as well as simultaneously, as applicable, it is possible to achieve relatively homogeneous spray coverage of large skin areas of arbitrary shape.

FIG. 6 shows a schematic view of a nozzle assembly where a single liquid outlet is symmetrically surrounded by four fluid outlets, all configured to eject gas and themselves conceptually arranged on the corners of a quadrilateral. Insofar, the nozzle assembly of FIG. 6 may be similar, or even identical, to nozzle assembly 7 shown in FIG. 1 and in particular FIG. 2. In this embodiment, the liquid outlet is connected to a liquid input W, and the fluid outlets are connected to corresponding gas inputs A1, A2, A3 and A4. There is a single source of pressurized gas which is connected to gas inputs A1, A2, A3 and A4 by means of four separate gas valves. However, it would be equally possible that each fluid outlet is connected to a separate source of pressurized gas, or that only some fluid outlets share a source of pressurized gas, whereas others are connected to their respective own source of pressurized gas. By closing and opening these gas valves, it is possible to change the area which is cooled by the spray. For example, if the laser scanner is adjusted to scan the laser beam only over areas S4 and S2 (as shown in FIG. 6), the gas valves may be controlled in such a manner that the spray is directed only to areas S4 and S2. In another embodiment, the cooled area may be synchronized with the laser scanner in such a manner that the area which is predominantly cooled tracks the area which is currently irradiated. Thus, if the scanned laser beam proceeds, e.g., from S1 to S4 during the scan, so does the scanned micro-pulsed spray.

Notably, the nozzle assembly of FIG. 6 comprises fluid outlets that are operable individually as well as simultaneously and that are arranged apart such that the atomized liquid spray they generate (or rather take part in generating) may not only cover portions S1 through S4 shown in FIG. 6, but also further portions that are not contained in (any combination of) S1 through S4 as will be explained in more detail further below. Specifically, as can be gathered from FIG. 6, the fluid outlets are each configured to eject gas in a different direction of motion, which different directions of motion however intersect in a point on a line extending perpendicularly from the liquid outlet of the nozzle assembly to the treatment area. Therein, the liquid outlet is arranged centrally in the nozzle assembly, symmetrically surrounded by the four fluid outlets. Put differently, the fluid outlets are thus arranged mutually cross-wise with respect to the respective portions of the treatment area. That is, a distance between a center of portion S1 and the first fluid outlet is larger than a distance between the center of portion S1 and the second fluid outlet, and a distance between a center of portion S2 and the second fluid outlet is larger than a distance between the center of portion S2 and the first fluid outlet, etc. Notably, said line extending perpendicularly from the liquid outlet to the treatment area is parallel to the direction of motion of the liquid stream that the liquid outlet is configured to eject (the same considerations would however apply mutatis mutandis if the liquid outlet was configured to eject the liquid, e.g., in the form of a drop dangling from the liquid outlet). Thus, a gas stream ejected from any of the fluid outlets impinges on the liquid stream, carrying the liquid stream with it, to generate an atomized liquid spray, which then, assuming individual operation of the respective fluid outlet, covers the corresponding portion of the treatment area.

It is however also possible that two or more fluid outlets are operated simultaneously. Since the directions of motion of the respective gas streams intersect, i.e., since the fluid outlets are arranged mutually cross-wise, these gas streams collide at a distance from the treatment area. In turn, these gas streams are deflected by each other, such that the atomized liquid spray generated using these gas streams covers parts of the treatment area that are not contained in (any combination of) portions S1 through S4, as will be discussed in further detail below with reference to FIG. 7.

In the embodiment of FIG. 6, the gas streams collide closer to the nozzle assembly than to the treatment area, at about a quarter of the total distance between the nozzle assembly and the treatment area. However, this may be different in other embodiments. It is generally possible that two or more gas streams, ejected from respective gas outlets, collide at any distance from the treatment area and/or the nozzle assembly. For example, gas streams may collide at a quarter, a third or half of the distance between the nozzle assembly and the treatment area, as viewed either from the nozzle assembly or the treatment area. If there are more than two gas streams colliding, there may also be multiple points of collision at different distances from the nozzle assembly and/or the treatment area.

In some embodiments, operation may alternate among individual or multiple ones of the plurality of valves in such a manner that either a pre-cooling or a post-cooling or both are performed for the treated tissue, e.g., when moving the laser beam across the treatment area. Generally, pre-cooling and/or post-cooling are performed at a time difference when compared with the cooling of the treatment area. Alternatively, the nozzle assembly with a plurality of fluid outlets, each configured to eject gas, may be operated in such a manner that only pre-cooling or post-cooling, or both are performed, but that no spray is applied to the area currently being irradiated.

In general, by closing and opening the gas valves for one or more of the fluid outlets (and assuming a suitable arrangement, e.g., orientation of the fluid outlets), it is possible to control the rate at which the spray is applied to an area and to select the part/portion of the tissue surface/treatment area which is to be cooled, i.e., covered by the fluid for cooling (here: the atomized liquid spray).

This may be understood based on FIG. 7, which provides a schematic view of different portions of a treatment area that the fluid for cooling, i.e., the spray, may cover depending on which fluid outlets of the nozzle assembly of FIG. 6 are operated: If only the first fluid outlet (connected to gas input A1) is operated, portion S1 of the treatment area is covered by the spray. If only the second fluid outlet (connected to gas input A2) is operated, portion S2 of the treatment area is covered by the spray (cf. also right panel of FIG. 4). If only the third fluid outlet (connected to gas input A3) is operated, portion S3 of the treatment area is covered by the spray. If only the fourth fluid outlet (connected to gas input A4) is operated, portion S4 of the treatment area is covered by the spray (cf. also left panel of FIG. 4). In FIG. 7, portions S1 through S4 do not mutually overlap at all, however, in other embodiments, this may be different, as discussed above. In fact, in FIG. 7, there are voids between portions S1 through S4 that are not covered by any spray, at least not as long as only the first through the fourth fluid outlet are operated individually. In FIG. 7, portions S1, S2, S3 and S4 comprise a round, e.g., circular shape and a similar, e.g., identical, diameter $d_1 = d_2 = d_3 = d_4$. Portions S1, S2, S3 and S4 also comprise similar, partly even identical distances to the respective other portions (it is reiterated that a distance between two portions may be defined as the minimum distance between any one point (on the perimeter) of the one portion and any one point (on the perimeter) of the other portion), i.e., $d_{\overline{12}} = d_{\overline{34}} < d_{\overline{23}} = d_{\overline{41}} < d_{\overline{13}} = d_{\overline{24}}$, wherein $0.25d_1 < d_{\overline{12}} = d_{\overline{34}} < 0.35d_1$, $0.45d_1 < d_{\overline{23}} = d_{\overline{41}} < 0.55d_1$ and $0.8d_1 < d_{\overline{13}} = d_{\overline{24}} < d$ (It is noted that this is different in the embodiment of FIG. 4, where the portions S1 through S4 each touch their two nearest neighbors).

These voids, i.e., the parts of the treatment area that are not covered by any spray as long as only individual fluid outlets are operated, may however be covered with spray by operating two or more fluid outlets simultaneously.

For example, if the first fluid outlet and the second fluid outlet are operated simultaneously, portion S12 of the treatment area is covered by the spray, wherein portion S12 of the treatment area lies partly in between portions S1 and S2 of the treatment area (i.e., portion S12 of the treatment area is not fully contained in portions S1 and/or S2 of the treatment area). If the second fluid outlet and the third fluid outlet are operated simultaneously, portion S23 of the treatment area is covered by the spray, wherein portion S23 of the treatment area lies partly in between portions S2 and S3 of the treatment area (i.e., portion S23 of the treatment area is not fully contained in portions S2 and/or S3 of the treatment area). If the third fluid outlet and the fourth fluid outlet are operated simultaneously, portion S34 of the treatment area is covered by the spray, wherein portion S34 of the treatment area lies partly in between portions S3 and S4 of the treatment area (i.e., portion S34 of the treatment area is not fully contained in portions S3 and/or S4 of the treatment area). If the fourth fluid outlet and the first fluid outlet are operated simultaneously, portion S41 of the treatment area is covered by the spray, wherein portion S41 of the treatment area lies partly in between portions S4 and S1 of the treatment area (i.e., portion S41 of the treatment area is not fully contained in portions S4 and/or S1 of the treatment area). In a similar manner, one could simultaneously operate the first outlet and the third outlet or the second fluid outlet and the fourth fluid outlet, such that portions S13 or S24 (both not shown in FIG. 7) of the treatment area would be covered by the spray, wherein portions S13 and S24 of the treatment area would lie at least partly in between portions S1 and S3 as well as S2 and S4 of the treatment area, respectively (i.e., portion S13 of the treatment area would not be fully contained in portions S1 and/or S3 of the treatment area, and portion S24 of the treatment area would not be fully contained in portions S2 and/or S4 of the treatment area). Therein, portions S12, S23, S34, S41, S13 and S24 at most partly overlap (i.e., they are not fully contained in one another or any combinations of the respective others). Portions S12 and S34 comprise a slightly elliptical, e.g., almost circular, shape, with diameter (defined as the maximum distance between any two points on their respective perimeter) $d_{12}=d_{34}>d_1=d_2=d_3=d_4$. Portions S23 and S41 comprise a more pronounced elliptical shape, with diameter $d_{23}=d_{41}>d_1=d_2=d_3=d_4$, but $d_{23}=d_{41}<d_{12}=d_{34}$. Diameters $d_{12}$, $d_{34}$ extend essentially perpendicularly to diameters $d_{23}$, $d_{41}$, i.e., portions S12 and S34 are oriented perpendicularly to portions S23 and S41 with respect to their major (i.e., longer) axes.

Yet further portions of the treatment area, which may neither be covered with spray upon individual operation of one or more single fluid outlets nor upon simultaneous operation of any two fluid outlets, could be covered with spray by operating three fluid outlets simultaneously. For example, if the first fluid outlet, the second fluid outlet and the third fluid outlet were operated simultaneously, portion S123 (not shown in FIG. 7) of the treatment area may be covered by the spray, wherein portion S123 of the treatment area lies at least partly in between portions S1, S2 and S3 of the treatment area (i.e., portion S123 of the treatment area is not fully contained in portions S1, S2 and/or S3 of the treatment area). Additionally, portion S123 of the treatment area may overlap at most partly with portions S12, S13 and S23 of the treatment area (i.e., portion S123 of the treatment area may not be fully contained in portions S12, S13 and/or S23 of the treatment area). If the second fluid outlet, the third fluid outlet and the fourth fluid outlet were operated simultaneously, portion S234 (not shown in FIG. 7) of the treatment area may be covered by the spray, wherein portion S234 of the treatment area lies at least partly in between portions S2, S3 and S4 of the treatment area (i.e., portion S234 of the treatment area is not fully contained in portions S2, S3 and/or S4 of the treatment area). Additionally, portion S234 of the treatment area may overlap at most partly with portions S23, S24 and S34 of the treatment area (i.e., portion S234 of the treatment area may not be fully contained in portions S23, S24 and/or S34 of the treatment area). If the third fluid outlet, the fourth fluid outlet and the first fluid outlet were operated simultaneously, portion S341 (not shown in FIG. 7) of the treatment area may be covered by the spray, wherein portion S341 of the treatment area lies at least partly in between portions S3, S4 and S1 of the treatment area (i.e., portion S341 of the treatment area is not fully contained in portions S3, S4 and/or S1 of the treatment area). Additionally, portion S341 of the treatment area may overlap at most partly with portions S34, S13, and S41 of the treatment area (i.e., portion S341 of the treatment area may not be fully contained in portions S34, S13 and/or S41 of the treatment area). If the fourth fluid outlet, the first fluid outlet and the second fluid outlet were operated simultaneously, portion S412 (not shown in FIG. 7) of the treatment area may be covered by the spray, wherein portion S412 of the treatment area lies at least partly in between portions S4, S1 and S2 of the treatment area (i.e., portion S412 of the treatment area is not fully contained in portions S4, S1 and/or S2 of the treatment area). Additionally, portion S412 of the treatment area may overlap at most partly with portions S41, S24, and S12 of the treatment area (i.e., portion S412 of the treatment area may not be fully contained in portions S41, S24 and/or S12 of the treatment area). Therein, portions S123, S234, S341 and S412 may at most partly overlap (i.e., they are not fully contained in one another or any combinations of the respective others).

Yet further portions of the treatment area, which may neither be covered with spray upon individual operation of one or more single fluid outlets nor upon simultaneous operation of any two or even three fluid outlets, could be covered with spray by operating all four fluid outlets simultaneously. That is, if the first fluid outlet, the second fluid outlet, the third fluid outlet and the fourth fluid outlet are operated simultaneously, portion S1234 of the treatment is covered by the spray, wherein portion S1234 of the treatment area lies at least partly in between portions S1, S2, S3 and S4 of the treatment area (i.e., portion S1234 of the treatment area is not fully contained in portions S1, S2, S3 and/or S4 of the treatment area). Additionally, portion S1234 of the treatment area may lie at least partly in between portions S12, S23, S34, S41, S13 and S24 of the treatment area (i.e., portion S1234 of the treatment area is not fully contained in portions S12, S23, S34, S41, S13 and/or S24 of the treatment area). Further additionally, portion S1234 of the treatment area may lie at least partly in between portions S123, S234, S341 and S412 of the treatment area (i.e., portion S1234 of the treatment area is not fully contained in portions S123, S234, S341 and/or S412 of the treatment area). Portions S1234 comprises a round, e.g., circular, shape with a diameter $d_{1234}\approx d_1=d_2=d_3=d_4$.

While, as apparent from the above, simultaneous operation of an additional fluid outlet generally results in additional parts or portions of the treatment area being covered by the spray, this does not mean that any and all combinations of fluid outlets must be operated simultaneously to cover a given target treatment area. For example, (almost) the entire rectangular target treatment area T of FIG. 7 may be covered with spray by covering portions S1, S2, S3, S4, S12, S23, S34, S41 and S1234 by individual and simultaneous operation of the resepctive one or more fluid outlets. Put differently, target treatment area T is (almost) fully contained in (the set union of) S1, S2, S3, S4, S12, S23, S34, S41 and S1234. Hence, there is no need to also cover portions S13, S14, S123, S234, S341 and/or S412 with spray by simultaneous operation of the respective fluid outlets.

As is clear from the above, using a nozzle assembly according to the present invention, treatment areas of different sizes and virtually arbitrary shapes may be efficiently covered with a fluid for cooling by individual and/or simultaneous, respectively, operation of suitable (combinations of) fluid outlets. For example, while FIG. 7 shows a rectangular target treatment area, covered using four fluid outlets, differently shaped target treatment areas may be covered using the same or a different number of fluid outlets. For example, a smaller rectangular target treatment area may well be covered using two fluid outlets, a triangular target treatment area may be covered using three fluid outlets, and more complicated target treatment areas may be covered using more than four fluid outlets.

Notably, a nozzle assembly according to the present invention may hence in particular also be used to scan a target treatment area, e.g., in synchronization with a laser beam acting thereon. Therein, the nozzle assembly may even be used to implement pre- and post-cooling. This shall exemplarily be explained based on the target treatment area T and the various portions as per FIG. 7. First, the spay may (only) cover the upper third of the rectangular target treatment area T with spray—as a form of pre-cooling—via portions S1, S2 and S12, e.g., by periodically repeating coverage of these portions according to the following pattern ("pre-pattern"): S1, S12, S2, S12. After a given time, the spray may then cover (virtually) the entire target treatment area T—as a form of (main) cooling—via portions S1, S2, S3, S4, S12, S23, S34, S41 and S1234, e.g., by periodically repeating coverage of these portions according to the following pattern: S1, S12, S2, S1234, S23, S3, S34, S4, S1, S12, S2, S23, S3, S34, S4, S1234, S41.

Therein, the operation of the cooling mechanism, e.g., the amount of liquid or the gas/liquid ratio, can be adjusted in response to the recorded temperature of the tissue after the treatment, wherein this temperature can be recorded using a temperature detector. The temperature detector could be also integrated into a thermal camera which would provide an additional visual aid for the laser operator.

Finally, the apparatus for cooling tissues using a micro-pulsed spray as described herein can be designed as a stand-alone unit which may be used together with different energy-based devices, or it may be integrated into a particular energy-based device. Further, said apparatus for cooling may be operated independently from the energy-based device, or it may be configured to receive certain control signals from the energy-based device. In the latter case, the release of the spray pulses from the apparatus for cooling can occur, for example, in synchronization (with respect to time and/or treatment area) with the delivery of the treatment energy.

The invention claimed is:

1. A nozzle assembly for cooling a treatment area with a fluid, comprising a first fluid outlet and a second fluid outlet operable individually as well as simultaneously and arranged apart such that the fluid covers:
   a first portion of the treatment area if only the first fluid outlet is operated;
   a second portion of the treatment area if only the second fluid outlet is operated, wherein the second portion is not fully contained in the first portion; and
   a third portion of the treatment area if both the first fluid outlet and the second fluid outlet are operated, wherein the third portion is not fully contained in the first portion and/or the second portion.

2. The nozzle assembly according to claim 1, wherein a distance between a center of the first portion and the first fluid outlet is larger than a distance between the center of the first portion and the second fluid outlet; and/or
   wherein a distance between a center of the second portion and the second fluid outlet is larger than a distance between the center of the second portion and the first fluid outlet.

3. The nozzle assembly according to claim 1, wherein the first fluid outlet and the second fluid outlet are arranged such that, if both the first fluid outlet and the second fluid outlet are operated, fluid ejected from the first fluid outlet collides with fluid ejected from the second fluid outlet at a distance from the treatment area, such that the fluid ejected from the first fluid outlet and the fluid ejected from the second fluid outlet form the fluid covering the third portion.

4. The nozzle assembly according to claim 1, wherein the fluid is an atomized liquid spray.

5. The nozzle assembly according to claim 4, wherein at least one of the first fluid outlet and the second fluid outlet is configured to eject the atomized liquid spray.

6. The nozzle assembly according to claim 4, wherein at least one of the first fluid outlet and the second fluid outlet is configured to eject gas such that the gas impinges upon a liquid to generate the atomized liquid spray.

7. The nozzle assembly according to claim 6, wherein the at least one of the first fluid outlet and the second fluid outlet is configured to eject the gas in a pulsed manner, at a pulse period of 10 ms to 5000 ms.

8. The nozzle assembly according to claim 6, comprising a liquid outlet configured to eject the liquid.

9. The nozzle assembly according to claim 8, wherein the liquid outlet is configured to eject the liquid in the form of a liquid stream.

10. The nozzle assembly according to claim 8, wherein the liquid outlet is configured to eject the liquid in the form of a drop dangling from the liquid outlet.

11. The nozzle assembly according to claim 10, wherein the liquid outlet is configured to eject the liquid at a rate of 0.001 ml/min to 30 ml/min.

12. The nozzle assembly according to claim 8, wherein the liquid outlet is located between the first fluid outlet and the second fluid outlet, preferably on a straight line extending from the first fluid outlet to the second fluid outlet.

13. The nozzle assembly according to claim 1, further comprising a third fluid outlet operable individually as well as simultaneously with the first fluid outlet and/or the second fluid outlet and arranged apart from the first fluid outlet and the second fluid outlet such that the fluid covers:
   a fourth portion of the treatment area if only the third fluid outlet is operated, wherein the fourth portion is not fully contained in the first portion and/or the second portion;
   a fifth portion of the treatment area if only the first fluid outlet and the third fluid outlet are operated, wherein the fifth portion is not fully contained in the first portion and/or the fourth portion;
   a sixth portion of the treatment area if only the second fluid outlet and the third fluid outlet are operated, wherein the sixth portion is not fully contained in the second portion and/or the fourth portion; and
   a seventh portion of the treatment area if only the first fluid outlet, the second fluid outlet and the third fluid outlet are operated, wherein the seventh portion is not fully contained in the first portion and/or the second portion and/or the fourth portion.

14. The nozzle assembly according to claim 13, further comprising a fourth fluid outlet operable individually as well as simultaneously with the first fluid outlet and/or the second fluid outlet and/or the third fluid outlet and arranged apart from the first fluid outlet, the second fluid outlet and the third fluid outlet such that the fluid covers:
   an eighth portion of the treatment area if only the fourth fluid outlet is operated, wherein the eighth portion is not fully contained in the first portion and/or the second portion and/or the fourth portion;
   a ninth portion of the treatment area if only the first fluid outlet and the fourth fluid outlet are operated, wherein the ninth portion is not fully contained in the first portion and/or the eighth portion;
   a tenth portion of the treatment area if only the second fluid outlet and the fourth fluid outlet are operated, wherein the tenth portion is not fully contained in the second portion and/or the eighth portion;
   an eleventh portion of the treatment area if only the third fluid outlet and the fourth fluid outlet are operated, wherein the eleventh portion is not fully contained in the fourth portion and/or the eighth portion;
   a twelfth portion of the treatment area if only the first fluid outlet, the second fluid outlet and the fourth fluid outlet are operated, wherein the twelfth portion is not fully contained in the first portion and/or the second portion and/or the eighth portion;

a thirteenth portion of the treatment area if only the first fluid outlet, the third fluid outlet and the fourth fluid outlet are operated, wherein the thirteenth portion is not fully contained in the first portion and/or the fourth portion and/or the eighth portion;

a fourteenth portion of the treatment area if only the second fluid outlet, the third fluid outlet and the fourth fluid outlet are operated, wherein the fourteenth portion is not fully contained in the second portion and/or the fourth portion and/or the eighth portion; and a fifteenth portion of the treatment area if only the first fluid outlet, the second fluid outlet, the third fluid outlet and the fourth fluid outlet are operated, wherein the fifteenth portion is not fully contained in the first portion and/or the second portion and/or the fourth portion and/or the eighth portion.

15. A method of cooling a treatment area with a fluid using a nozzle assembly according to claim 1, comprising:

operating at least one of the first fluid outlet and the second fluid outlet individually; and operating the first fluid outlet and the second fluid outlet simultaneously.

16. The nozzle assembly according to claim 6, wherein the at least one of the first fluid outlet and the second fluid outlet is configured to eject the gas in a pulsed manner, at a pulse period of 100 ms to 2000 ms.

17. The nozzle assembly according to claim 6, wherein the at least one of the first fluid outlet and the second fluid outlet is configured to eject the gas in a pulsed manner, at a pressure of 0.1 bar to 20 bar.

18. The nozzle assembly according to claim 6, wherein the at least one of the first fluid outlet and the second fluid outlet is configured to eject the gas in a pulsed manner, at a pressure of 1 bar to 10 bar.

19. The nozzle assembly according to claim 10, wherein the liquid outlet is configured to eject the liquid at a rate of 0.2 ml/min to 4 ml/min.

* * * * *